United States Patent [19]

Reifschneider

[11] 4,413,009

[45] Nov. 1, 1983

[54] N-((ALKYLAMINO)CARBONYL)-N-(((ALKYLAMINO)CARBONYL)OXY)ACYLAMIDES WITH ANTINEOPLASTIC ACTIVITY

[75] Inventor: Walter Reifschneider, Walnut Creek, Calif.

[73] Assignee: The Dow Chemical Company, Midland, Mich.

[21] Appl. No.: 349,502

[22] Filed: Feb. 17, 1982

[51] Int. Cl.³ ............... A61K 31/215; A61K 31/325
[52] U.S. Cl. ............................. 424/298; 260/545 R
[58] Field of Search ............... 260/545 R, 453 RW; 424/315, 298; 564/39, 42, 44, 45

[56] References Cited

U.S. PATENT DOCUMENTS

| 3,836,572 | 9/1974 | Franz | 260/465 E |
| 3,957,867 | 5/1976 | Bukowick | 260/465.4 |
| 4,030,912 | 6/1977 | Bukowick | 71/120 |
| 4,207,091 | 6/1980 | Fischer | 71/113 |

OTHER PUBLICATIONS

Ogawa, Masami et al. *Chemical Abstracts,* vol. 86 (1977) #101,869w.

*Primary Examiner*—Natalie Trousof
*Assistant Examiner*—L. Hendriksen
*Attorney, Agent, or Firm*—Edward P. Gray; Ronald G. Brookens

[57] ABSTRACT

The present invention is directed to N-((alkylamino)-carbonyl)-N-(((alkylamino)carbonyl)oxy)acylamides and their use in inhibiting the growth of HeLa cells, $P_{388}$ leukemia or MX-1 carcinomas in mammals.

8 Claims, No Drawings

N-((ALKYLAMINO)CARBONYL)-N-(((ALKYLAMINO)CARBONYL)OXY)ACYLAMIDES WITH ANTINEOPLASTIC ACTIVITY

SUMMARY OF THE INVENTION

The present invention is directed to a group of novel organic compounds corresponding to the formula:

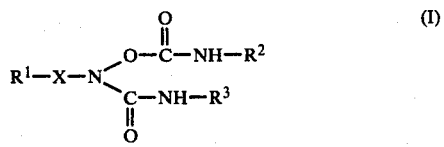

wherein $R^1$, $R^2$, and $R^3$ may each independently represent hydrogen, lower alkyl, cycloalkyl, phenyl or lower alkyl substituted phenyl; and X may be carbonyl

or sulfonyl ($-SO_2-$).

As used herein, the term "lower alkyl" refers to aliphatic, straight or branched chain radicals of from one to about four carbon atoms inclusive such as methyl, ethyl, isopropyl, tert-butyl and the like; the term "cycloalkyl" refers to saturated monocyclic hydrocarbon radicals of from three to about six carbon atoms, both inclusive, such as cyclopropyl, cyclohexyl and the like.

Preferred compounds of the present invention are those compounds of formula I in which $R^1$, $R^2$, and $R^3$ are each lower alkyl, and X is carbonyl or sulfonyl. Especially preferred are compounds wherein $R^1$, $R^2$, and $R^3$ are each methyl and X is carbonyl or sulfonyl. Particularly preferred is the compound in which $R^1$, $R^2$, and $R^3$ are each methyl and X is carbonyl.

The compounds of the present invention have been found to be effective in inhibiting the cellular growth, in mammals, of HeLa cells. In addition, the compounds have been found effective in inhibiting the growth of $P_{388}$ leukemia(s) or MX-1 carcinoma(s) in a mammal afflicted therewith.

The present invention is further directed to compositions suitable for inhibiting the growth of HeLa cells, $P_{388}$ leukemias or MX-1 carcinomas which contain an effective amount of the active compound or compounds as described herein in combination with a pharmaceutically-acceptable carrier.

DETAILED DESCRIPTION OF THE INVENTION

The compounds of the present invention may be readily prepared by the following methods.

(A) Those compounds of formula I wherein X is carbonyl and $R^1$, $R^2$ and $R^3$ have the significance previously given, and $R^2$ and $R^3$ are the same substituent may be prepared by reacting an $R^1$-substituted-acylhydroxamic acid of the formula:

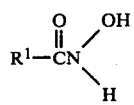

with a substituted isocyanate whose substituent is that selected for each of $R^2$ and $R^3$ in formula I.

For this reaction, good results are obtained when the substituted isocyanate is present in a molar concentration of about two times that of the $R^1$-substituted-acylhydroxamic acid. However, the amount of the reactants used is not critical and some of the desired product will be obtained when the reactants are employed in any proportion.

The reactants are contacted with one another in an inert organic solvent such as methylene chloride or tetrahydrofuran in the presence of a small amount of activating agent such as dibutyltin dilaurate or triethylamine. The reaction mixture is conveniently stirred at about room temperature under atmospheric pressure for a period of time sufficient to assure substantial completion of the reaction, and to obtain the desired product. It may also be necessary to use higher or lower temperatures, or employ an elevated pressure to insure completion of the reaction.

At the completion of the reaction, the solvent is removed from the reaction mixture by conventional techniques such as evaporation, filtration or decantation. Purification of the product is accomplished by procedures well known in the art, such as recrystallization.

(B) Those compounds of formula I wherein X is carbonyl and $R^1$, $R^2$ and $R^3$ have the significance previously given, and $R^2$ and $R^3$ represent different moieties are prepared by employing an essentially two-step procedure. In the first step, an acylhydroxamic acid as represented by formula II is reacted with an approximately equimolar amount of an isocyanate substituted with one of the moieties previously defined for $R^2$. At the completion of this reaction, the resulting product is reacted with an approximately equimolar amount of an isocyanate substituted with one of the moieties previously defined for $R^3$, leaving the desired compound of formula I.

While the exact proportion of the reactants employed is not critical, each step of this two-step procedure consumes the reactants in amounts representing essentially equimolar proportions, and the use of such amounts is preferred.

The above reactions are conveniently carried out employing reaction conditions substantially the same as those previously described in (A) above. These compounds are also recovered and purified utilizing conventional techniques as set forth in (A) above.

(C) Those compounds of formula I wherein X is sulfonyl and $R^1$, $R^2$, and $R^3$ have the significance previously given, and $R^2$ and $R^3$ are the same substituent are prepared in a manner substantially the same and under conditions and proportions substantially the same as that described in (A) above. A desired N-hydroxy-$R^1$-substituted sulfamide of the formula:

is reacted with an isocyanate whose substituent is that selected for each of $R^2$ and $R^3$ in formula I, wherein the molar concentration of the substituted isocyanate may be about two times that of the N-hydroxy-$R^1$-substituted sulfamide of formula III.

(D) Similarly, those compounds of formula I wherein X is sulfonyl, $R^1$, $R^2$, and $R^3$ have the significance previously given, and $R^2$ and $R^3$ represent different moieties are prepared in a manner substantially the same, and under conditions and proportions substantially the same as that described in (B) above. A desired N-hydroxy-$R^1$-substituted sulfamide of formula III is reacted with an approximately equimolar amount of an isocyanate substituted with one of the moieties previously defined for $R^2$. At the completion of this reaction, the resulting product is reacted with an approximately equimolar amount of an isocyanate substituted with one of the moieties previously defined for $R^3$, leaving the desired compound of formula I.

The compounds employed as starting materials in preparing the compounds of the present invention are all known in the art.

The following examples are set forth as a means of illustrating the present invention. They are specific examples of preferred embodiments and are not intended as a limitation on the invention.

EXAMPLE 1

N-((Methylamino)carbonyl)-N-(((methylamino)carbonyl)oxy)acetamide

A mixture of acetohydroxamic acid (7.5 grams), methyl isocyanate (12.0 grams), 80 milliliters (ml) of methylene chloride, and about three drops of triethylamine were stirred together for about one hour in order to obtain solution. The solution was allowed to stand at room temperature overnight after which the solvent was removed under vacuum, leaving a residue. The residue was recrystallized from methylene chloride leaving the desired N-((methylamino)carbonyl)-N-(((methylamino)carbonyl)oxy)acetamide as white crystals having a melting point (m.p.) of 121°-123.5° C.

EXAMPLE 2

N-((Ethylamino)carbonyl)-N-(((ethylamino)-carbonyl)oxy)acetamide

Acetohydroxamic acid (7.5 grams), ethyl isocyanate (16.0 grams), and about three drops of triethylamine were stirred in about 50 ml of methylene chloride for about 48 hours. The mixture was then concentrated under vacuum leaving a residue. This residue was recrystallized twice from a solution of methylene chloride and hexane, and then from a small amount of methylene chloride. A final recrystallization from toluene yielded the desired, N-((ethylamino)-carbonyl)-N-(((ethylamino)carbonyl)oxy)acetamide as white crystals, m.p. 84°-86° C.

EXAMPLE 3

N-(((1,1-dimethylethyl)amino)carbonyl)-N-((((1,1-dimethylethyl)amino)carbonyl)oxy)acetamide Acetohydroxamic acid (7.5 grams), tert-butyl isocyanate (22 grams) and a few drops of triethylamine were stirred in 80 ml of methylene chloride for about 48 hours. After stirring, the solvent was removed under vacuum leaving a residue which was recrystallized from a solution containing methylene chloride and hexane. A subsequent recrystallization from methylene chloride left the desired, N-(((1,1-dimethylethyl)amino)carbonyl)-N-((((1,1-dimethylethyl)amino)carbonyl)oxy)acetamide, m.p. 111°-113° C.

EXAMPLE 4

N-((methylamino)carbonyl)-N-(((methyl-amino)carbonyl)oxy)propionamide

Propiohydroxamic acid (4.5 grams), methyl isocyanate (6.0 grams), and a few drops of triethylamine were stirred for about one hour in about 50 ml of methylene chloride. The resulting solution was allowed to stand at room temperature for about 48 hours, after which the solvent was removed by evaporation leaving a residue. The residue was recrystallized from a mixture of methylene chloride and hexane leaving the desired, N-((methylamino)carbonyl)-N-(((methylamino)carbonyl)oxy)propionamide as white crystals, m.p. 90.5°-92.5° C.

EXAMPLE 5

N-((ethylamino)carbonyl)-N-(((ethylamino)-carbonyl)oxy)propionamide

Propiohydroxamic acid (4.5 grams), ethyl isocyanate (8.0 grams), and a few drops of triethylamine were added to 100 ml of methylene chloride and allowed to stand at room temperature for about 12 hours. The solvent was then removed under vacuum leaving a residue which was recrystallized from a solution of methylene chloride and hexane leaving the desired, N-((ethylamino)carbonyl)-N-(((ethylamino)carbonyl)oxy)propionamide as white crystals, m.p. 104°-106° C.

EXAMPLE 6

N-((Methylamino)carbonyl)-N-(((methylamino)-carbonyl)oxy)(2,2-dimethyl)propionamide (2,2-dimethyl)propiohydroxamic acid (5.9 grams), methyl isocyanate (6.5 grams), and a few drops of triethylamine were stirred in about 50 ml of methylene chloride over a period of about 48 hours. This mixture was then concentrated under vacuum leaving a colorless, oily residue. Trituration of this oil with hexane left a sticky solid which was recrystallized from a solution of methylene chloride and hexane. Subsequent recrystallization from a minimal amount of methylene chloride and toluene left the desired, N-((methylamino)carbonyl)-N-((methylamino)carbonyl)oxy)(2,2-dimethyl)propionamide as white crystals, m.p. 117°-119° C. (with slight sintering from about 116° C.).

Following a procedure substantially the same as that described above, the following compounds were prepared by reacting an appropriate substitued acylhydroxamic acid with an appropriate isocyanate.

EXAMPLE 7

N-(((Cyclohexylamino)carbonyl)-N-(((cyclohexylamino)carbonyl)oxy)acetamide, m.p. 109°–112° C.

EXAMPLE 8

N-(((1-Methylethyl)amino)carbonyl)-N-((((1-methylethyl)amino)carbonyl)oxy)acetamide, m.p. 65°–68° C.

EXAMPLE 9

N-((Propylamino)carbonyl)-N-(((propylamino)carbonyl)oxy)acetamide, m.p. 50°–53° C.

EXAMPLE 10

N-((Phenylamino)carbonyl)-N-(((phenylamino)carbonyl)oxy)acetamide, m.p. 134°–136° C.

EXAMPLE 11

N-(((3-methylphenyl)amino)carbonyl)-N-((((3-methylphenyl)amino)carbonyl)oxy)acetamide.

EXAMPLE 12

N-(((4-Methylphenyl)amino)carbonyl)-N-((((4-methylphenyl)amino)carbonyl)oxy)acetamide, m.p. 140°–142° C.

EXAMPLE 13

N-((Butylamino)carbonyl)-N-(((butylamino)carbonyl)oxy)acetamide.

EXAMPLE 14

N-(((1-Methylethyl)amino)carbonyl)-N-((((1-methylethyl)amino)carbonyl)oxy)benzamide.

EXAMPLE 15

N-((Methylamino)carbonyl)-N-(((methylamino)-carbonyl)oxy)benzamide, m.p. 131°–133° C.

EXAMPLE 16

N-((Ethylamino)carbonyl)-N-(((ethylamino)-carbonyl)oxy)benzamide, m.p. 154°–155° C.

EXAMPLE 17

N-((Propylamino)carbonyl)-N-(((propylamino)-carbonyl)oxy)benzamide, m.p. 66°–69° C.

EXAMPLE 18

N-((Butylamino)carbonyl)-N-(((butylamino)-carbonyl)oxy)benzamide, m.p. 42°–43° C.

EXAMPLE 19

N-(((1,1-Dimethylethyl)amino)carbonyl)-N-((((1,1-dimethylethyl)amino)carbonyl)oxy)benzamide, m.p. 133°–134° C.

EXAMPLE 20

N-((Phenylamino)carbonyl)-N-(((phenyl-amino)carbonyl)oxy)benzamide.

EXAMPLE 21

N-((Methylamino)carbonyl)-N-((((1,1-dimethylethyl)amino)carbonyl)oxy)acetamide (a) N-((((1,1-dimethylethyl)amino)carbonyl)oxy)-acetamide Acetohydroxamic acid (7.5 grams) tert-butyl isocyanate (10.0 grams) and a few drops of triethylamine were stirred at room temperature in about 200 ml of methylene chloride for 3 hours. After this period of time, an insoluble solid from the reaction was collected by filtration and was determined to be the desired product. The filtrate was concentrated under vacuum leaving a residue which was recrystallized from toluene leaving an additional quantity of the desired, N-((((1,1-dimethylethyl)amino)carbonyl)oxy)acetamide.

(b) N-((methylamino)carbonyl)-N-((((1,1-dimethylethyl)amino)carbonyl)oxy)acetamide N-((((1,1-dimethylethyl)amino)carbonyl)oxy)acetamide (8.7 grams), methyl isocyanate (3.2 grams), and a few drops of triethylamine were stirred at room temperature in 150 ml of methylene chloride for about 12 hours. The solvent was then removed under vacuum leaving an oily residue which was dissolved in hot toluene. Upon cooling, a white crystalline material separated and was collected by filtration. The white crystals were recrystallized from toluene leaving a residue which was mixed with about 50 ml of water for two hours. This mixture was then filtered, and the insoluble material was dried in a vacuum leaving the desired N-((methylamino)carbonyl)-N-((((1,1-dimethylethyl)amino)carbonyl)oxy)acetamide, m.p. 142°–144° C.

EXAMPLE 22

N-((Propylamino)carbonyl)-N-(((propyl-amino)carbonyl)oxy)cyclopropanecarboxamide (a) Preparation of N-hydroxycyclopropanecarboxamide A solution of about 1.3 moles of hydroxylamine hydrochloride in about 500 ml of methanol was prepared and cooled. To this was added 300 ml of a methanol solution containing about 2.0 moles of potassium hydroxide. After about five minutes, ethyl cyclopropanecarboxylate (0.66 mole) was added. This reaction mixture was filtered about 10 minutes later leaving a residue which was washed with methanol and subsequently acidified. The acidified mixture was filtered, and the filtrate was concentrated leaving a solid. The solid was recrystallized from ethyl acetate leaving a white solid determined to be N-hydroxycyclopropanecarboxamide, m.p. 117°–119° C.

(b) N-((propylamino)carbonyl)-N-(((propylamino)carbonyl)oxy)cyclopropanecarboxamide N-hydroxycyclopropanecarboxamide (5.0 grams), n-propyl isocyanate (9.3 grams) and 5 drops of triethylamine were stirred at room temperature in about 100 ml of methylene chloride for about 12 hours. The reaction mixture was then concentrated leaving an oily residue which crystallized upon scratching. This solid was then recrystallized from a mixture of cyclohexane and isopropanol and dried. Upon drying, the desired N-((propylamino)carbonyl)-N-(((propylamino)carbonyl)oxy)cyclopropanecarboxamide was obtained as a white solid, m.p. 76°–78° C.

Utilizing a substantially similar procedure, the following compounds were prepared.

EXAMPLE 23

N-((Methylamino)carbonyl)-N-(((methylamino)carbonyl)oxy)cyclopropanecarboxamide, m.p. 109°–111° C.

EXAMPLE 24

N-((Ethylamino)carbonyl)-N-(((ethylamino)carbonyl)oxy)cyclopropanecarboxamide, m.p. 120°–122° C.

EXAMPLE 25

N-(((1-Methylethyl)amino)carbonyl)-N-((((1-methylethyl)amino)carbonyl)oxy)cyclopropanecarboxamide, m.p. 99°–101° C.

EXAMPLE 26

N-((Butylamino)carbonyl)-N-(((butylamino)carbonyl)oxy)cyclopropanecarboxamide, m.p. 48°–49° C.

EXAMPLE 27

N-(((1,1-Dimethylethyl)amino)carbonyl)-N-((((1,1-dimethylethyl)amino)carbonyl)oxy)cyclopropanecarboxamide.

EXAMPLE 28

N-((Phenylamino)carbonyl)-N-(((phenylamino)carbonyl)oxy)cyclopropanecarboxamide, m.p. 140°–142° C.

EXAMPLE 29

N-((Cyclohexylamino)carbonyl)-N-(((cyclohexylamino)carbonyl)oxy)cyclopropanecarboxamide, m.p. 122°–124° C.

EXAMPLE 30

N-((Methylamino)carbonyl)-N-(((methyl-amino)carbonyl)oxy)methanesulfamide (a) Preparation of N-hydroxymethanesulfamide A solution of sodium methoxide was prepared by dissolving 23 grams of sodium in 300 ml of methanol. This solution was added (with cooling) to 69 grams of hydroxylamine hydrochloride in 300 ml of methanol and subsequently filtered. The filtrate was cooled to about 15° C. and methanesulfonyl chloride (19.3 ml) was added. After about 48 hours, the reaction mixture was filtered, and the filtrate was concentrated leaving a residue. The residue was extracted four times with diethyl ether and the combined ether extracts were concentrated to leave a light, yellow viscous oil. A white solid formed upon scratching which had infrared absorptions consistent with the desired N-hydroxymethanesulfamide.

(b) N-((methylamino)carbonyl)-N-(((methylamino)carbonyl)oxy)methanesulfamide

N-Hydroxymethanesulfamide (8.0 grams), methylisocyanate (9.4 ml) and about five drops of triethylamine were contacted in about 80 ml of methylene chloride. As the reaction proceeded a white solid was formed and subsequently recovered. The solid was recrystallized from isopropanol leaving the desired N-((methylamino)-carbonyl)-N-(((methylamino)carbonyl)oxy)methanesulfamide, m.p. 131°–132° C.

Following a procedure essentially the same as that in Example 30, the following compound was made.

EXAMPLE 31

N-((Ethylamino)carbonyl)-N-(((ethylamino)-carbonyl)oxy)-methanesulfamide

The physical properties of the compounds of formula I are set forth in Table 1.

TABLE 1

| Compound Example Number | $R^1$ | $R^2$ | $R^3$ | X | M.P. (°C.) | Yield (%) | Calculated %C | %H | %N | Found %C | %H | %N |
|---|---|---|---|---|---|---|---|---|---|---|---|---|
| 1 | $CH_3$ | $CH_3$ | $CH_3$ | $-\overset{O}{\underset{\|}{C}}-$ | 121.5–123.5 | 91 | 38.09 | 5.86 | 22.21 | 38.16 | 5.75 | 22.22 |
| 2 | $CH_3$ | $C_2H_5$ | $C_2H_5$ | $-\overset{O}{\underset{\|}{C}}-$ | 84–86 | 45 | 44.23 | 6.96 | 19.35 | 44.43 | 7.04 | 19.50 |
| 3 | $CH_3$ | $C(CH_3)_3$ | $C(CH_3)_3$ | $-\overset{O}{\underset{\|}{C}}-$ | 111–113 | 96 | 53.73 | 8.48 | 15.37 | 53.20 | 8.44 | 15.47 |
| 4 | $C_2H_5$ | $CH_3$ | $CH_3$ | $-\overset{O}{\underset{\|}{C}}-$ | 90.5–92.5 | 90 | 41.37 | 6.45 | 20.68 | 41.38 | 6.40 | 20.70 |
| 5 | $C_2H_5$ | $C_2H_5$ | $C_2H_5$ | $-\overset{O}{\underset{\|}{C}}-$ | 104–106 | 84 | 46.74 | 7.41 | 18.17 | 46.78 | 7.26 | 18.15 |
| 6 | $C(CH_3)_3$ | $CH_3$ | $CH_3$ | $-\overset{O}{\underset{\|}{C}}-$ | 117–119 | 33 | 46.74 | 7.41 | 18.17 | 46.92 | 7.28 | 18.35 |
| 7 | $CH_3$ | $C_6H_5$ | $C_6H_5$ | $-\overset{O}{\underset{\|}{C}}-$ | 109–112 | 63 | 59.06 | 8.37 | 12.91 | 58.9 | 8.44 | 12.81 |
| 8 | $CH_3$ | $-CH(CH_3)_2$ | $-CH(CH_3)_2$ | $-\overset{O}{\underset{\|}{C}}-$ | 65–68 | 65 | 48.97 | 7.81 | 17.13 | 48.0 | 7.72 | 17.25 |

TABLE 1-continued

| Compound Example Number | R¹ | R² | R³ | X | M.P. (°C.) | Yield (%) | Calculated % C | % H | % N | Found % C | % H | % N |
|---|---|---|---|---|---|---|---|---|---|---|---|---|
| 9 | CH₃ | —(CH₂)₂CH₃ | —(CH₂)₂CH₃ | $\underset{-C-}{\overset{O}{\|}}$ | 50–53 | 76 | 48.97 | 7.81 | 17.13 | 48.4 | 7.79 | 17.18 |
| 10 | CH₃ | Ph— | Ph— | $\underset{-C-}{\overset{O}{\|}}$ | 134–136 | 71 | 61.33 | 4.83 | 13.41 | 61.5 | 4.99 | 13.43 |
| 11 | CH₃ | o-CH₃-C₆H₄— | o-CH₃-C₆H₄— | $\underset{-C-}{\overset{O}{\|}}$ | 99–102 | 54 | 63.33 | 5.61 | 12.31 | 63.4 | 5.77 | 12.41 |
| 12 | CH₃ | p-CH₃-C₆H₄— | p-CH₃-C₆H₄— | $\underset{-C-}{\overset{O}{\|}}$ | 140–142 | 75 | 63.33 | 5.61 | 12.31 | 63.3 | 5.76 | 12.24 |
| 13 | CH₃ | —(CH₂)₃CH₃ | —(CH₂)₃CH₃ | $\underset{-C-}{\overset{O}{\|}}$ | | 26 | 48.27 | 8.10 | 16.08 | 49.3 | 8.72 | 16.18 |
| 14 | Ph— | —CH(CH₃)₂ | —CH(CH₃)₂ | $\underset{-C-}{\overset{O}{\|}}$ | | 40 | | | | | | |
| 15 | Ph— | CH₃ | CH₃ | $\underset{-C-}{\overset{O}{\|}}$ | 131–133 | 67 | 52.59 | 5.18 | 16.73 | 52.59 | 5.33 | 16.50 |
| 16 | Ph— | C₂H₅ | C₂H₅ | $\underset{-C-}{\overset{O}{\|}}$ | 154–155 | 54 | 55.9 | 6.14 | 15.05 | | | |
| 17 | Ph— | —(CH₂)₂CH₃ | —(CH₂)₂CH₃ | $\underset{-C-}{\overset{O}{\|}}$ | 66–69 | 43 | 58.62 | 6.89 | 13.67 | 58.54 | 6.99 | 13.61 |
| 18 | Ph— | —(CH₂)₃CH₃ | —(CH₂)₃CH₃ | $\underset{-C-}{\overset{O}{\|}}$ | 42–43 | 52 | 60.85 | 7.51 | 12.53 | 60.71 | 7.63 | 12.53 |
| 19 | Ph— | —C(CH₃)₃ | —C(CH₃)₃ | $\underset{-C-}{\overset{O}{\|}}$ | 133–134 | 8 | | | | | | |
| 20 | Ph— | Ph— | Ph— | $\underset{-C-}{\overset{O}{\|}}$ | | | | | | | | |
| 21 | CH₃ | —C(CH₃)₃ | CH₃ | $\underset{-C-}{\overset{O}{\|}}$ | 142–144 | | 46.74 | 7.41 | 18.17 | 46.38 | 7.06 | 18.33 |
| 22 | cyclopropyl | —(CH₂)₂CH₃ | —(CH₂)₂CH₃ | $\underset{-C-}{\overset{O}{\|}}$ | 76–78 | 88 | 53.16 | 7.80 | 15.49 | 53.1 | 7.82 | 15.72 |
| 23 | cyclopropyl | CH₃ | CH₃ | $\underset{-C-}{\overset{O}{\|}}$ | 109–111 | 74 | 44.65 | 6.09 | 19.53 | 44.6 | 6.21 | 19.71 |
| 24 | cyclopropyl | C₂H₅ | C₂H₅ | $\underset{-C-}{\overset{O}{\|}}$ | 120–122 | 82 | 49.37 | 7.05 | 17.27 | 49.5 | 7.10 | 17.42 |
| 25 | cyclopropyl | —CH(CH₃)₂ | —CH(CH₃)₂ | $\underset{-C-}{\overset{O}{\|}}$ | 99–101 | 62 | 53.16 | 7.80 | 15.49 | 53.0 | 7.91 | 15.55 |
| 26 | cyclopropyl | —(CH₂)₃CH₃ | —(CH₂)₃CH₃ | $\underset{-C-}{\overset{O}{\|}}$ | 48–49 | 78 | 56.17 | 8.42 | 14.04 | 56.0 | 8.34 | 13.87 |
| 27 | cyclopropyl | —C(CH₃)₃ | —C(CH₃)₃ | $\underset{-C-}{\overset{O}{\|}}$ | | 41 | | | | | | |
| 28 | cyclopropyl | Ph— | Ph— | $\underset{-C-}{\overset{O}{\|}}$ | 140–142 | 43 | 63.71 | 5.05 | 12.38 | 63.6 | 5.02 | 12.37 |

TABLE 1-continued

| Compound Example Number | R¹ | R² | R³ | X | M.P. (°C.) | Yield (%) | Calculated %C | %H | %N | Found %C | %H | %N |
|---|---|---|---|---|---|---|---|---|---|---|---|---|
| 29 | cyclopropyl | phenyl(H) | phenyl(H) | $-\overset{O}{\underset{\|}{C}}-$ | 122–124 | 52 | 61.51 | 8.32 | 11.96 | 62.1 | 8.44 | 11.91 |
| 30 | $CH_3$ | $CH_3$ | $CH_3$ | $-\overset{O}{\underset{\underset{O}{\|}}{\overset{\|}{S}}}-$ | 131–132 | 55 | 26.67 | 4.93 | 18.66 | | | |
| 31 | $CH_3$ | $C_2H_5$ | $C_2H_5$ | $-\overset{O}{\underset{\underset{O}{\|}}{\overset{\|}{S}}}-$ | | | | | | | | |

EXAMPLE 32

The compounds of this invention exhibit the property of inhibiting cell growth of HeLa cells (a human carcinoma of the cervix). This activity was demonstrated utilizing the following procedures:

HeLa cells were seeded in 24-well tissue culture plates at a concentration of 30 cells per well in 1 ml of growth medium (Eagle's minimum essential medium with 5 percent HIFCS). The plates were incubated at 36° C. for 24 hours after which the growth medium was removed. The cells were resuspended in 1 ml of fresh growth medium described above together with a measured quantity of (0–50 μg/ml) of one of the compounds of this invention. The 0 μg/ml concentration served as a control. The tissue culture plates were then incubated at 36° C. for 8 days at which time the medium was removed and the cells were fixed and stained with 0.1% crystal violet in 20% ethanol. The HeLa cell colonies were counted macroscopically, and comparisons of colony size in treated and control wells were made. Test compounds were considered cytotoxic at concentrations which reduced the number of HeLa cell colonies compared to control by 50% or more. Test compounds of the invention were considered to cause HeLa cell growth inhibition at concentrations which reduced the size of colonies by a measurable amount when compared to control. The results of this test are set forth in Table 2, below.

TABLE 2

| Compound Example No. | Cytotoxicity[1] | Cell Growth Inhibition[2] |
|---|---|---|
| 1 | 50 | 12.5 |
| 2 | 12.5 | 12.5 |
| 3 | 12.5 | 12.5 |
| 4 | 50 | 12.5 |
| 5 | 50 | 50 |
| 6 | 12.5 | 12.5 |
| 7 | 6.3 | 1.6 |
| 8 | 1.6 | 1.6 |
| 9 | 6.3 | 6.3 |
| 10 | 50 | 50 |
| 11 | 12.5 | 50 |
| 12 | 12.5 | 12.5 |
| 13 | 3.1 | 3.1 |
| 14 | 3.1 | 0.8 |
| 15 | 12.5 | 3.1 |
| 16 | 12.5 | 12.5 |
| 17 | 50 | 12.5 |
| 18 | 3.1 | 0.8 |
| 19 | 50 | 50 |
| 20 | 50 | 50 |
| 22 | 12.5 | 3.1 |
| 23 | 12.5 | 12.5 |
| 24 | 3.1 | 3.1 |
| 25 | 3.1 | 3.1 |
| 26 | 12.5 | 12.5 |
| 27 | 50 | 50 |
| 28 | 50 | 50 |
| 29 | 12.5 | 12.5 |
| 30 | 12.5 | 3.1 |
| 31 | 3.1 | 3.1 |

[1] Concentration (μg/ml) at which the number of colonies of HeLa cells were reduced by 50% or more (as compared to control).
[2] Concentration (μg/ml) at which the size of the HeLa colonies were reduced by a measurable amount (as compared to control).

EXAMPLE 33

The compounds of formula I are useful in the treatment of certain mammalian tumors; in particular $P_{388}$ leukemia and/or MX-1 carcinoma.

Antineoplastic activity for the subject compounds was demonstrated utilizing the following testing procedures:

(A) Test mice ($CDF_1$ mice) were injected intraperitoneally (IP) with ascitic fluid containing $10^6$ cells of $P_{388}$ lymphocytic leukemia. The test compound was administered in a sialine -Tween 80 carrier at the appropriate dosage, IP daily for 9 days; the initial treatment performed the first day after tumor inoculation. Control mice received no compound. Survival times of the treated and untreated (control mice were noted. The results, $$\frac{\text{Median survival time of treated group}}{\text{Median survival time of control group}} \times 100,$$

are expressed as a percentage of the control survival time (T/C%). Therefore, a value greater than 100 shows an increase in the median survival time of the treated group as compared to the control group.

TABLE 3

| | Activity Against $P_{388}$ Leukemia | | | | |
|---|---|---|---|---|---|
| | | Experiment No. 1 | | Experiment No. 2 | |
| Compound Example Number | Dose[1] (mg/kg) | T/C % | Toxicity[2] Day Survivors | T/C % | Toxicity[2] Day Survivors |
| 1 | 200.00 | | 00/06 | NT | NT |
| | 100.00 | | 01/06 | | 03/06 |
| | 50.00 | 142 | 06/06 | 141 | 06/06 |

TABLE 3-continued

Activity Against P$_{388}$ Leukemia

| Compound Example Number | Dose[1] (mg/kg) | Experiment No. 1 | | Experiment No. 2 | |
|---|---|---|---|---|---|
| | | T/C % | Toxicity[2] Day Survivors | T/C % | Toxicity[2] Day Survivors |
| | 25.00 | NT | NT | 126 | 06/06 |
| | 12.50 | NT | NT | 131 | 06/06 |

[1]The symbol (mg/kg) represents milligrams/kilogram of body weight per injection.
[2]The numerator of the fraction indicates the number of mice which survived to toxicity day (that is, the day specified by the tester upon which the toxicity evaluation is made) and the denominator indicates the number of mice which originally started treatment. Excessive deaths (generally >34%) at a particular dosage is an indication that the compound is toxic to the test animal at that dosage.
NT = Not Tested.

The data presented in Table 3 indicates that N-((methylamino)carbonyl)-N-(((methylamino)carbonyl)-oxy)acetamide (compound) increased the median survival time of the test mice afflicted with P$_{388}$ leukemia.

The compound increased the median survival time of the test animals at dosages of 50 milligrams/kilogram of body weight (mg/kg) per injection in one experiment and at 12.50, 25 and 50 mg/kg in another experiment. Excessive deaths or excessive weight loss on toxicity day in an otherwise inactive test are indications of toxicity in a survival model or false activity in tumor inhibition models.

(B) A tumor fragment (MX-1 human breast xenograft) having a diameter of between 9 and 12 ocular micrometer units (OMU) (approximately 1×1×1 millimeter) was implanted and measured in situ in the subrenal capsule of athymic Swiss (Nu/Nu Swiss) mice. The appropriate dosage of the test compound in a saline carrier was administered by subcutaneous injection once daily for 10 days; the initial treatment was performed on the first day after tumor implant. No test compound was administered to the control mice. Test mice were sacrificed on the eleventh day and tumor size noted. The change in tumor diameter (from day 0 (implant day) to day 11 (sacrifice day)) as compared with the tumor size of the control was used as an evaluation of tumor growth or regression.

TABLE 4

Activity Against MX-1 Human Breast Xenograft

| Experiment Number | Compound of Example Number I | Dose[1] (mg/kg) | Toxicity Day[2] Survivors | Δ t[3] | Δ c[4] |
|---|---|---|---|---|---|
| 1 | Control | | | | 5.09 |
| | | 100 | 01/03 | −0.33 | |
| | | 50 | 03/03 | −0.19 | |
| | | 25 | 03/03 | 0.44 | |
| | | 12.5 | 03/03 | 7.25 | |
| 2 | Control | | | | 18.34 |
| | | 200 | 05/06 | 0.46 | |
| | | 100 | 06/06 | 0.69 | |
| | | 50 | 06/06 | 5.60 | |
| | | 25 | 06/06 | 19.46 | |
| 3 | Control | | | | 11.15 |
| | | 200 | 00/06 | −0.53 | |
| | | 100 | 06/06 | −0.18 | |
| | | 50 | 06/06 | 0.27 | |
| | | 25 | 06/06 | 9.91 | |
| 4 | Control | | | | 6.29 |
| | | 200 | 01/03 | −0.32 | |
| | | 100 | 03/03 | 0.07 | |
| | | 50 | 02/02 | 5.64 | |
| | | 25 | 03/03 | 4.53 | |

[1]The symbol (mg/kg) represents milligrams/kilogram of body weight per injection.
[2]The numerator of the fraction indicates the number of mice which survived to toxicity day (that is, the day specified by the tester upon which the toxicity evaluation is made) and the denominator inidicates the number of mice which originally started treatment. Excessive deaths (generally >34%) at a particular dosage is an indication that the compound is toxic to the test animal at that dosage.
[3]Negative values represent the mean decrease in tumor size (of the stated weight in milligrams) for the treated mice from the day of implant to the day of sacrifice. Positive values represent the mean increase in tumor size (of the stated weight in milligrams) for the treated mice from the day of implant to the day of sacrifice.
[4]The value stated represents the mean tumor weight (in milligrams) for the control mice on sacrifice day.

The data presented in Table 4 indicate that the compounds of the present invention show excellent activity against MX-1 carcinoma over a substantial dosage range. Treatment with these compounds not only slow the growth rate of the tumor but in some instances the compounds can reduce the tumor size.

The compounds can be administered to mammals parenterally, for example, by intraperitoneal, subcutaneous or intravenous injection. The route of internal administration should be selected to ensure that an effective antineoplastic amount (i.e., growth inhibiting amount) of the compound contacts the tumor(s).

The exact amount of the compound or compounds to be employed in practicing the method of the present invention, i.e., the amount of the compound or compounds sufficient to provide the desired tumor growth inhibitory effect, depends upon various factors such as the compound or compounds employed; type of contacting or administration; the size, age and species of mammal; the route, time and frequency of administration and the neoplasm involved. In particular cases, the amount to be administered can be determined by conventional range finding techniques.

The compounds are preferably administered internally or topically in the form of a composition comprising one or more compounds corresponding to formula I in admixture with a pharmaceutically-acceptable carrier, i.e., a carrier which is chemically inert to the active compound and which has no detrimental side effects or toxicity under the conditions of use, such as saline or pyrogen-free water.

The compositions can be in liquid forms such as sterile injectable suspensions or solutions. The pharmaceutically-acceptable carriers can include excipients such as surface active dispensing agents and suspending agents. Suitable excipients are disclosed, for example, in texts such as Remington's Pharmaceutical Manufacturing, Thirteenth Edition, Mack Publishing Co., Easton, PA (1965).

What is claimed is:

1. A composition useful for inhibiting the growth of P$_{388}$ leukemia or MX-1 carcinoma comprising a pharmaceutically-acceptable carrier in combination with an effective P$_{388}$ leukemia or MX-1 carcinoma inhibiting amount of a compound corresponding to the formula

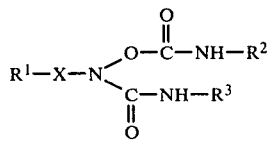

(I)

wherein $R^1$, $R^2$ and $R^3$ may each independently represent hydrogen, alkyl of 1 to 4 carbon atoms, cycloalkyl of from 3 to 6 carbon atoms, phenyl or phenyl substituted with from 1 to 5 alkyl groups of 1 to 4 carbon atoms and X represents carbonyl or sulfonyl.

2. A composition as defined in claim 1 wherein X is carbonyl.

3. A composition as defined in claim 2 wherein $R^1$, $R^2$ and $R^3$ are each alkyl.

4. The composition of claim 3 wherein the compound is N-((methylamino)carbonyl)-N-(((methylamino)carbonyl)oxy)acetamide.

5. A method for inhibiting the growth of $P_{388}$ leukemia or MX-1 carcinoma in a mammal afflicted therewith which comprises administering to said mammal, in an amount effective to inhibit said growth, a compound corresponding to the formula

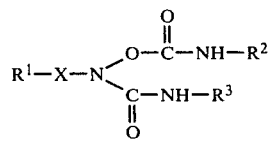

(I)

wherein $R^1$, $R^2$ and $R^3$ may each independently represent hydrogen, alkyl of 1 to 4 carbon atoms, cycloalkyl of from 3 to 6 carbon atoms, phenyl or phenyl substituted with from 1 to 5 alkyl groups of 1 to 4 carbon atoms and X represents carbonyl or sulfonyl in admixture with a pharmaceutically-acceptable carrier therefor.

6. A method as defined in claim 5 wherein X is carbonyl.

7. A method as defined in claim 6 wherein $R^1$, $R^2$ and $R^3$ are each alkyl.

8. The method of claim 7 wherein the compound is N-((methylamino)carbonyl)-N-(((methylamino)carbonyl)oxy)acetamide.

* * * * *